US008844360B2

(12) United States Patent
Knowles et al.

(10) Patent No.: US 8,844,360 B2
(45) Date of Patent: Sep. 30, 2014

(54) METHOD FOR CHECKING THE MECHANICAL INTEGRITY OF STABILIZING ELEMENTS ON THE ROTOR BLADES OF A TURBINE AND SCANNING DEVICE FOR IMPLEMENTING THE METHOD

(75) Inventors: James Knowles, Baden (CH); Peter Schott, Trautskirchen (DE); Pascal Maibach, Neuenhof (CH)

(73) Assignee: ALSTOM Technology Ltd, Baden (CH)

( * ) Notice: Subject to any disclaimer, the term of this patent is extended or adjusted under 35 U.S.C. 154(b) by 134 days.

(21) Appl. No.: 13/197,828

(22) Filed: Aug. 4, 2011

(65) Prior Publication Data
US 2012/0073375 A1    Mar. 29, 2012

(30) Foreign Application Priority Data
Aug. 4, 2010 (DE) .......................... 10 2010 033 302

(51) Int. Cl.
*G01N 29/04* (2006.01)
(52) U.S. Cl.
USPC .............................................. 73/618; 73/620
(58) Field of Classification Search
USPC ........... 73/625, 618, 620, 622, 626, 602, 583, 73/596, 598, 600
See application file for complete search history.

(56) References Cited

U.S. PATENT DOCUMENTS

| 4,257,743 A | 3/1981 | Fujii | |
|---|---|---|---|
| 4,297,885 A * | 11/1981 | Hein et al. | 73/587 |
| 4,502,331 A * | 3/1985 | Singh et al. | 73/627 |
| 5,275,052 A * | 1/1994 | Luttrell et al. | 73/619 |
| 5,280,723 A * | 1/1994 | Aharoni et al. | 73/602 |
| 5,670,879 A | 9/1997 | Zombo et al. | |
| 6,857,330 B2 | 2/2005 | Murphy et al. | |
| 7,075,296 B2 | 7/2006 | Moore | |
| 7,093,491 B2 * | 8/2006 | Murphy et al. | 73/620 |
| 7,302,851 B2 * | 12/2007 | Czerw et al. | 73/620 |
| 8,347,724 B2 * | 1/2013 | Brignac | 73/639 |

(Continued)

FOREIGN PATENT DOCUMENTS

DE    102008359836 A1    6/2010
EP        1462610 A1    9/2004

(Continued)

OTHER PUBLICATIONS

Katsuhiro Onda et al., Development of Phased Array UT System for Turbine Blades Inspection, The Japanese Society for Non-Destructive Inspection, Sep. 1989, vol. 38, No. 9A, pp. 841-842.

(Continued)

*Primary Examiner* — Helen Kwok

(57) ABSTRACT

A method for checking a mechanical integrity of at least two stabilizing elements includes providing the at least two stabilizing elements that mechanically interconnect blade airfoils of rotor blades of a turbine in a circumferential direction of the turbine in an installed state of the turbine. The at least two stabilizing elements are adjacent to one another and inter-engage to form an engagement section having a material volume of the at least two stabilizing elements in the engagement section. The material volume of the at least two stabilizing elements is scanned, in an automated manner using ultrasound, so as to determine whether cracks are present. The scanning is performed from an outside of the at least two stabilizing elements.

18 Claims, 4 Drawing Sheets

(56) References Cited

U.S. PATENT DOCUMENTS

| | | | |
|---|---|---|---|
| 8,376,710 B2* | 2/2013 | Gerber et al. | 416/190 |
| 2004/0191068 A1 | 9/2004 | Richter et al. | |
| 2006/0283250 A1 | 12/2006 | Fair et al. | |
| 2008/0245151 A1* | 10/2008 | Roney et al. | 73/628 |
| 2008/0250860 A1* | 10/2008 | Clossen-von Lanken Schulz et al. | 73/627 |
| 2009/0126493 A1 | 5/2009 | Moore et al. | |
| 2009/0229365 A1* | 9/2009 | Bentzel | 73/627 |
| 2010/0135775 A1 | 6/2010 | Masserey et al. | |
| 2010/0150726 A1* | 6/2010 | Rose et al. | 416/220 R |

FOREIGN PATENT DOCUMENTS

| | | |
|---|---|---|
| JP | 61-15560 | 1/1986 |
| JP | 10-231702 | 9/1998 |
| JP | 2008-82992 | 4/2008 |
| WO | WO 2006101586 A1 | 9/2006 |

OTHER PUBLICATIONS

Notification of Reasons for Refusal (Type 1 Office Action)—Japanese Patent Applm. No. 2011-170362, dated Jun. 30, 2014.

* cited by examiner

US 8,844,360 B2

METHOD FOR CHECKING THE MECHANICAL INTEGRITY OF STABILIZING ELEMENTS ON THE ROTOR BLADES OF A TURBINE AND SCANNING DEVICE FOR IMPLEMENTING THE METHOD

CROSS REFERENCE TO PRIOR APPLICATIONS

Priority is claimed to German Patent Application No. DE 10 2010 033 302.6, filed Aug. 4, 2010, the entire disclosure of which is incorporated by reference herein.

TECHNICAL FIELD

The present invention relates to the field of non-destructive material testing in the field of turbines. It refers to a method for checking the mechanical integrity of stabilizing elements on the rotor blades of a turbine according to the preamble of claim 1 and a scanning device for implementing the method.

BACKGROUND OF THE INVENTION

Steam turbines, particularly in the low pressure range, are equipped with rotor blades of long length which, if no suitable countermeasures are adopted, are prone to undesirable vibrations during operation. A countermeasure is to provide a mechanical connection between the blade airfoils of the rotor blades in the region of the blade tip, as described in DE 102008059836A1, for example.

Such connections may be made by means of special stabilizing elements in a center region of the blade airfoils, as is described in printed publication U.S. Pat. No. 4,257,743.

In FIG. 1, a connection is shown in a detail. The rotor blades 11 of a steam turbine 10 there have in each case a through-hole 13, through which an arc-shaped stabilizing element 12 is inserted and soldered with hard solder, the shape of the stabilizing element being shown in FIG. 2 in plan view from above (FIG. 2a) and in side view (FIG. 2b).

The stabilizing elements 12 of FIGS. 1 and 2 are all of a similar design. They have in each case two end sections 18 and 19. The first end section 18 is formed as V-shaped groove (also referred to as a "notch") with two groove walls 20, and the second end section 19, which matches it, is formed as a V-shape wedge with inclined walls 22 (also referred to as an "iron sight"). Arranged between the end sections 18, 19, in the middle, is a thickened center piece 15 from which arms 16, 17 extend to the end sections 18, 19. The stabilizing elements 12, which are arranged one behind the other in the circumferential direction, engage in each case by their second end section 19 in the first end section 18 of the subsequent stabilizing element, as is shown by way of example in FIG. 3. In this way, an engagement section 14, which is marked by means of the dashed circle in FIG. 3, is created between two consecutive stabilizing elements 12a, 12b. The engagement section 14 is delimited on the oppositely-disposed outer sides by means of two planar outer surfaces 21. Since the blade is twisted, the iron sight always buts against the notch on one side only (installed side). If the blade untwists during operation, the iron sight buts against the notch by the other side (operating side).

In the case of the installed stabilizing elements 12 or 12a, 12b cracks may occur in the engagement section 14 during operation, the cracks occurring mainly on the notch side, i.e. in the groove walls 20 of the first end sections 18, and therefore are not visible from the outside in the first instance.

In principle, a crack inspection of the engagement section 14 by MPI methods (Magnetic Particle Inspection) may be undertaken. These methods, however, have the disadvantage that cracks can be detected only if they occur on the outside, which as a rule is too late in order to be able to exchange defective elements in good time (major consequential damage).

It would also be conceivable to inspect the engagement section 14 manually by means of ultrasound. Such a manual inspection could certainly detect cracks earlier, but on account of the confined space conditions between the rotor blades 11 is difficult, time-consuming and not very reliable.

SUMMARY OF THE INVENTION

In an embodiment, the present invention provides a method for checking a mechanical integrity of at least two stabilizing elements including providing the at least two stabilizing elements that mechanically interconnect blade airfoils of rotor blades of a turbine in a circumferential direction of the turbine in an installed state of the turbine. The at least two stabilizing elements are adjacent to one another and inter-engage to form an engagement section having a material volume of the at least two stabilizing elements in the engagement section. The material volume of the at least two stabilizing elements is scanned, in an automated manner using ultrasound, so as to determine whether cracks are present. The scanning is performed from an outside of the at least two stabilizing elements.

BRIEF DESCRIPTION OF THE DRAWINGS

The present invention will be described in even greater detail below based on the exemplary figures. The invention is not limited to the exemplary embodiments. Other features and advantages of various embodiments of the present invention will become apparent by reading the following detailed description with reference to the attached drawings which illustrate the following.

DETAILED DESCRIPTION

Figure 1:
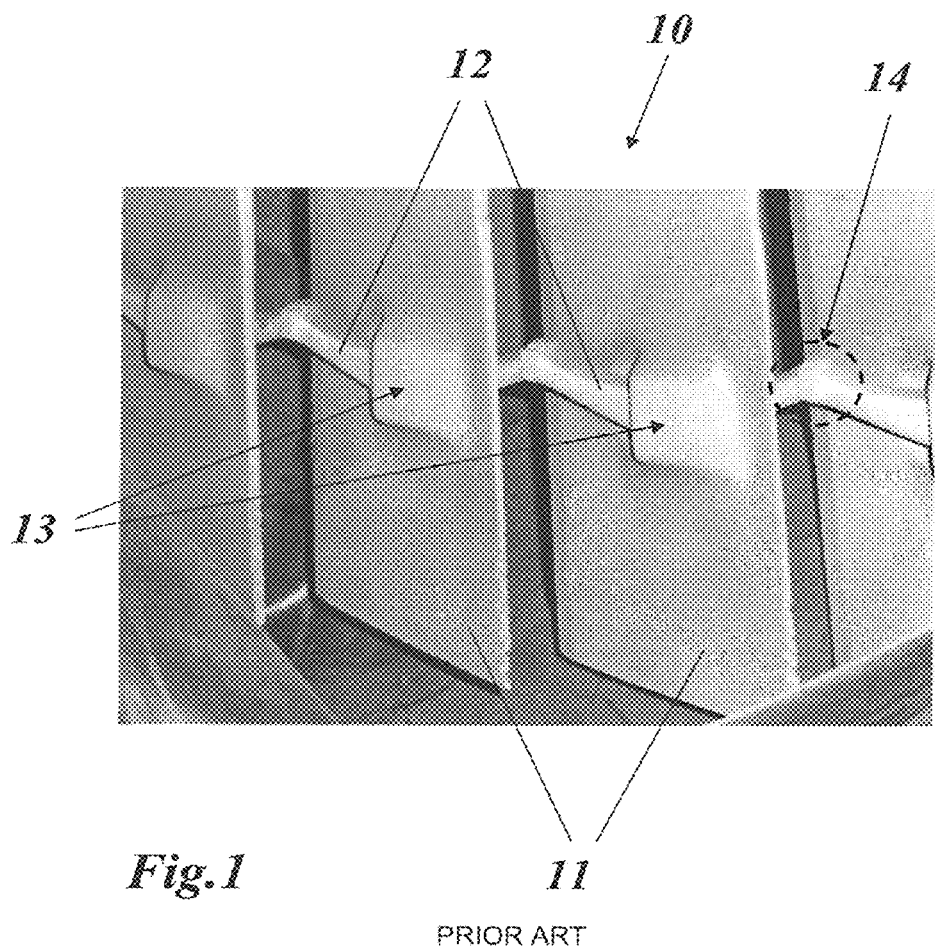
FIG. 1 shows in a detail a plurality of rotor blades of a steam turbine, the blade airfoils of which are mechanically interconnected via stabilizing elements.
Figure 2:
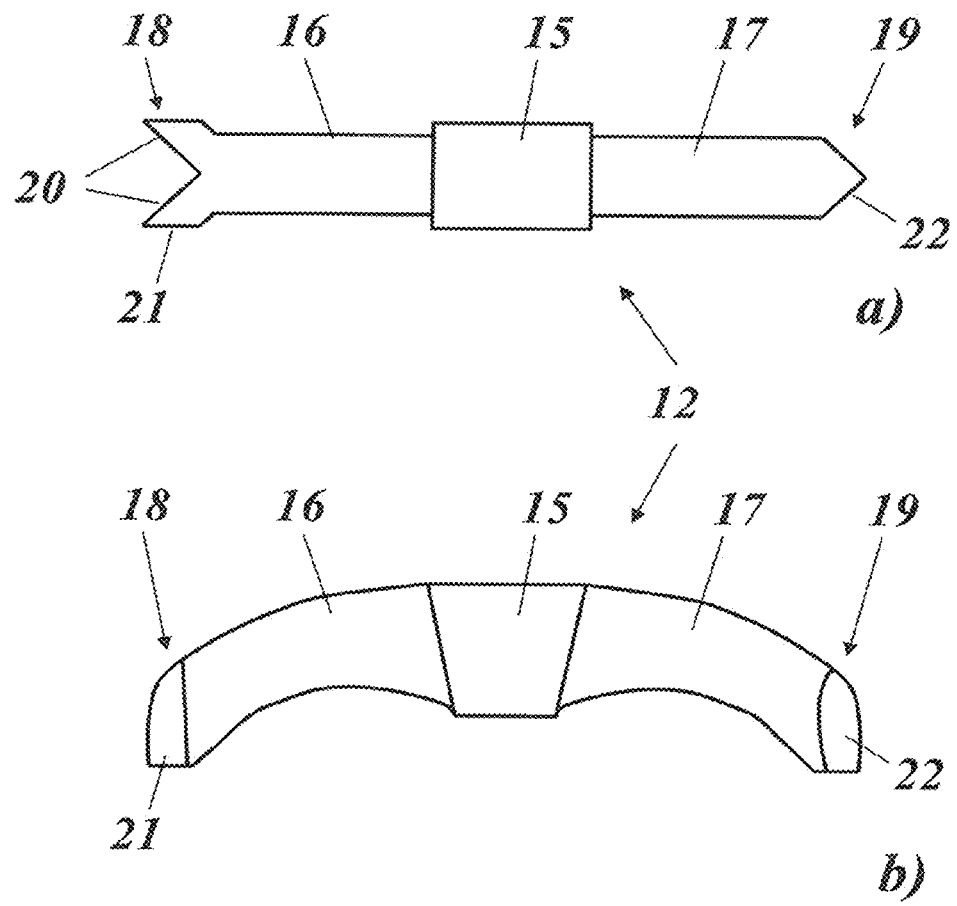
FIG. 2 shows the configuration of an individual stabilizing element from FIG. 1 in plan view from above (FIG. 2a) and in side view (FIG. 2b)

An aspect of the invention is to provide a method which avoids the disadvantages of the known methods and which is fast, reproducible and provides reliable results, and to provide a scanning device for implementing the method.

In an embodiment of the invention, the material volume of the stabilizing elements which is located in the engagement section is automatically scanned from the outside by ultrasound for the presence of cracks.

In an embodiment of the invention, the stabilizing elements are delimited in the engagement section on the outside by means of planar outer surfaces, and in that the scanning is carried out along the outer surfaces.

In another embodiment of the invention, the scanning is carried out in the radial direction.

In another embodiment of the invention, the scanning is carried out with one or more ultrasonic beams that are coupled into the engagement section or into the outer surfaces at an oblique incidence angle.

In an embodiment of the invention, the scanning is carried out on opposite sides of the engagement section at the same time.

In an embodiment of the invention, the scanning location is continuously determined, and the scanning location and scanning result are correlated with each other and stored in the correlation.

The scanning device according to the invention for implementing the method comprises at least one sensor for ultrasonic scanning, and also first means for fixing the scanning device on the stabilizing elements in the engagement section and second means for the automatic moving of the at least one sensor along the engagement section.

In an embodiment, the scanning device includes at least one sensor that is a single-channel ultrasonic sensor.

In another embodiment, the scanning device includes at least one sensor that is a phased-array signal converter.

In a further embodiment, the scanning device includes at least one sensor that is mounted on the scanning device in an articulated manner for adapting to the outer surfaces of the stabilizing elements. As a result of this, an automatic and secure abutment of the sensors against the planar outer surfaces can be achieved.

In an embodiment, the scanning device includes two sensors, which are disposed opposite each other and are provided for the simultaneous scanning of the engagement section from opposite sides. As a result of this, the inspection can be accelerated considerably.

In another embodiment, each sensor of the scanning device comprises two or more signal converters which emit ultrasonic beams at different angles. As a result of this, a more accurate determination of possible cracks is achieved.

In particular, the ultrasonic beams are inclined relative to the seating surface of the sensor in this case.

Another embodiment of the scanning device according to the invention includes second means that comprise a preferably motor-driven movement mechanism.

In another embodiment of the scanning device according to the invention, provision is made on the scanning device for means of the continuous determination of the position of the at least one sensor during the scanning process. As a result of this, the results can be graphically represented in a simple manner.

In an embodiment, the scanning device includes first means that have clamps for the releasable, preferably self-centering, fixing of the scanning device on the stabilizing elements.

Another embodiment of the scanning device according to the invention includes first means which comprise retaining magnets.

Figures 3, 4:
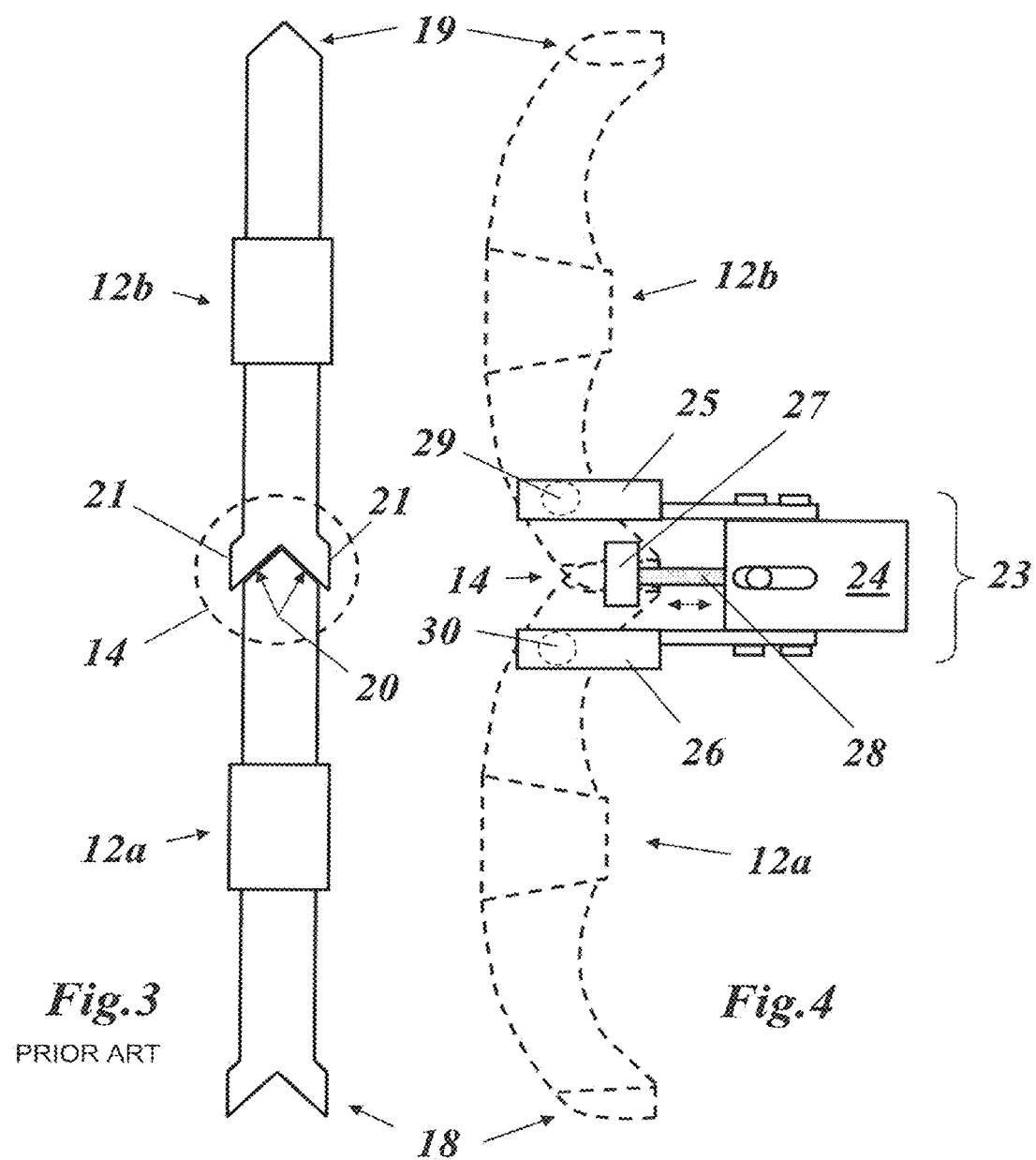
FIG. 3 shows in plan view from above the inter-engagement of two stabilizing elements according to FIG. 2, forming an engagement section.
FIG. 4 shows in side view a scanning device, seated upon the stabilizing elements, for scanning the engagement section according to an exemplary embodiment of the invention.

FIG. 4 shows in side view a scanning device 23, which is seated upon the stabilizing elements 12a, 12b (identified by dashed lines), for scanning the engagement section 14 according to an exemplary embodiment of the invention. The scanning device 23 has a housing 24 in which is accommodated and guided a movement mechanism 28 with which a sensor 27, which is attached on the front end of the movement mechanism 28, can be moved back and forth in a controlled manner in the radial direction, with regard to the turbine axis, for the ultrasound inspection. If the movement mechanism 28 is driven by means of an electric motor, for example, this is accommodated inside the housing 24. Not shown in FIG. 4 is a cable which extends from the housing 24 and contains power supply leads and signal leads.

U-shaped clamps 25, 26 are attached on the housing 24 of the scanning device 23 on opposite sides, with which the scanning device 23, clamping on both sides of the engagement section 14, can be pushed and fixed on the adjoining arms 16, 17 of the stabilizing elements 12a, 12b which overlap in the engagement section 14. For additional fixing, provision may be made in the region of the clamps 25, 26 for retaining magnets 29, 30 which assist the clamping forces of the clamps 25, 26.

Figure 6:
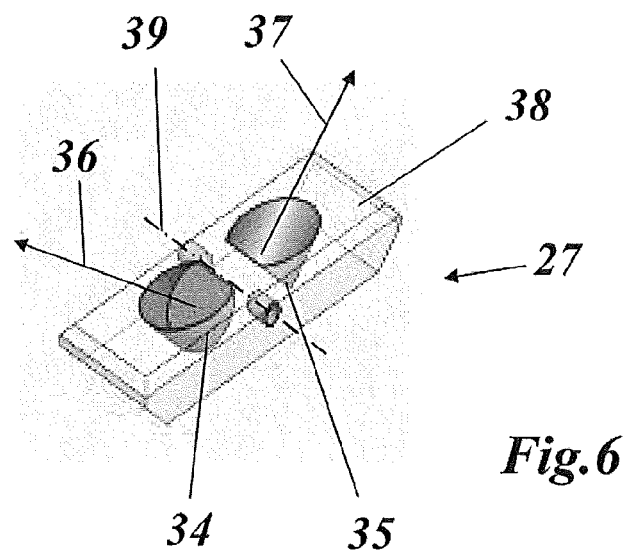
FIG. 6 shows in a perspective side view a sensor for use in a scanning device according to FIG. 4, which generates two ultrasonic beams which are inclined to each other and to the seating surface.

The ultrasonic waves which are transmitted from the sensor 27 and also received again are coupled in and coupled out over the planar outer surfaces 21 of the engagement section 14. So that this coupling in and coupling out can be optimally carried out, the sensor 27 must lie by its seating surface (38 in FIG. 6) as extensively as possible on the respective outer surface 21. In order to make this easier, the sensor 27 is attached on the end of the movement mechanism 28 preferably in an articulated manner, for example cardanically or pivotably around an axis (39 in FIG. 6).

In order to shorten the scanning process, a corresponding sensor 27 can be provided for each of the outer surfaces 21. The scanning with ultrasound is then carried out from opposite sides at the same time. According to FIG. 6, each sensor 27 can comprise two or more signal converters 34, 35 which operate according to the pulse-echo principle and emit ultrasonic beams 36, 37 at different angles. In particular, the ultrasonic beams 36, 37 can be inclined relative to the seating surface 38 of the sensor 27 in this case. The sensor 27, however, can also be a phased-array signal converter, the ultrasonic beam of which can be pivoted by altering the phase relationship.

It is advantageous if the scanning device is provided with position sensors which during the scanning process continuously detect the position of the sensor, or sensors 27, so that the corresponding scanning result can be correlated with each sensor position and in the evaluation a two-dimensional representation of the scanning results is possible.

Figure 5:
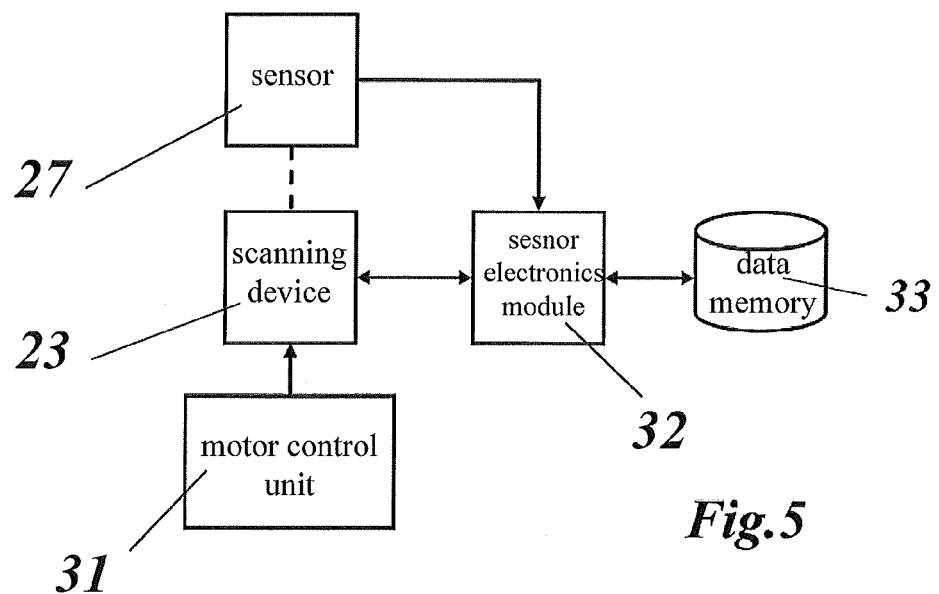
FIG. 5 shows an exemplary block schematic for the operation of a scanning device according to FIG. 4.

For controlling the scanning process, a block diagram according to FIG. 5 is suitable. A motor control unit 31, which at the same time also includes a power supply for the motorized drive, is connected via a cable to the scanning device 23. The control unit 31 controls the movement of the movement mechanism 28 and therefore the scanning path of the sensor 27. An external sensor electronics module 32 is connected to the sensor 27 and obtains from there the corresponding scanning signals.

Furthermore, the sensor electronics module 32 obtains from the scanning device 23 the determined position values of the sensor 27. Both variables, interlinked, are stored in a data memory 33 and can be retrieved for graphic representation of the result or for comparison with other results.

While the invention has been described with reference to particular embodiments thereof, it will be understood by those having ordinary skill the art that various changes may be made therein without departing from the scope and spirit of the invention. Further, the present invention is not limited to the embodiments described herein; reference should be had to the appended claims.

LIST OF REFERENCE NUMERALS

10 Turbine (steam turbine)
11 Rotor blade
12, 12a, b Stabilizing element (arc)
13 Through-hole
14 Engagement section
15 Center piece
16, 17 Arm
18, 19 End section (groove-form, wedge-form)
20 Groove wall
21 Outer surface
22 Wedge wall
23 Scanning device (scanner)
24 Housing
25, 26 Retaining means (clamps, for example)
27 Sensor
28 Movement mechanism
29, 30 Retaining magnet
31 Motor control unit
32 Sensor electronics module
33 Data memory
34, 35 Signal converter
36, 37 Ultrasonic beam
38 Seating surface
39 Axis

What is claimed is:

1. A method for checking a mechanical integrity of at least two stabilizing elements comprising:
   providing the at least two stabilizing elements, which mechanically interconnect blade airfoils of rotor blades of a turbine in a circumferential direction of the turbine in an installed state of the turbine, the at least two stabilizing elements being adjacent to one another and inter-engaging to form an engagement section having a material volume of the at least two stabilizing elements in the engagement section; and
   scanning, in an automated manner using ultrasound, the material volume so as to determine whether cracks are present, the scanning being performed from an outside of the at least two stabilizing elements along planar outer surfaces of the at least two stabilizing elements which delimits the at least two stabilizing elements in the engagement section.

2. The method as recited in claim 1, wherein the turbine is a steam turbine.

3. The method as recited in claim 1, wherein the scanning is performed in a radial direction of the turbine.

4. The method as recited in claim 1, wherein the scanning is performed using at least one ultrasonic beam coupled into at least one of the engagement section and the planar outer surfaces at an oblique incidence angle.

5. The method as recited in claim 1, wherein the scanning is performed on opposite sides of the engagement section at the same time.

6. The method as recited in claim 1, wherein the scanning includes continuously determining a scanning location, correlating the scanning location and a scanning result with each other so as to obtain a correlation and storing the correlation.

7. A scanning device for scanning at least two stabilizing elements for cracks, the at least two stabilizing elements mechanically interconnecting blade airfoils of rotor blades of a turbine in a circumferential direction of the turbine and being adjacent to one another and inter-engaging to form an engagement section of the at least two stabilizing elements, the scanning device comprising:
   at least one sensor configured to ultrasonically scan the at least two stabilizing elements from an outside of the at least two stabilizing elements so as to determine whether cracks are present;
   a fixing device configured to fix the scanning device on one of the at least two stabilizing elements in the engagement section; and
   a moving device configured to move the at least one sensor along the engagement section.

8. The scanning device as recited in claim 7, wherein the at least one sensor includes a single-channel ultrasonic sensor.

9. The scanning device as recited in claim 7, wherein the at least one sensor includes a phased-array signal converter.

10. The scanning device as recited in claim 7, wherein the at least one sensor is disposed on the scanning device in an articulated manner so as to adapt to an outer surface of each of the at least two stabilizing elements.

11. The scanning device as recited in claim 7, wherein the at least one sensor includes two sensors disposed opposite each other that are configured to simultaneously scan opposite sides of the engagement section.

12. The scanning device as recited in claim 7, wherein the at least one sensor includes at least two signal converters, each of the signal converters being configured to emit an ultrasonic beam that are at different angles relative to one another.

13. The scanning device as recited in claim 12, wherein the ultrasonic beams are inclined relative to a seating surface of the at least one sensor.

14. The scanning device as recited in claim 7, wherein the moving device is a motor-driven movement mechanism.

15. The scanning device as recited in claim 7, further comprising a position determination device configured to continuously determine a position of the at least one sensor during the scanning.

16. The scanning device as recited in claim 7, wherein the fixing device includes a clamp configured to releasably fix the scanning device on one of the at least two stabilizing elements.

17. The scanning device as recited in claim 16, wherein the clamp is configured to self-center the scanning device on one of the at least two stabilizing elements.

18. The scanning device as recited in claim 7, wherein the fixing device includes a retaining magnet.

* * * * *